United States Patent
Shang

(10) Patent No.: US 10,594,112 B1
(45) Date of Patent: Mar. 17, 2020

(54) INTERVENTION PHOTON CONTROL METHOD AND DEVICE

(71) Applicant: Hua Shang, Shanghai (CN)

(72) Inventor: Hua Shang, Shanghai (CN)

( * ) Notice: Subject to any disclaimer, the term of this patent is extended or adjusted under 35 U.S.C. 154(b) by 0 days.

(21) Appl. No.: 16/396,998

(22) Filed: Apr. 29, 2019

(51) Int. Cl.
| | | |
|---|---|---|
| *H01S 3/10* | (2006.01) | |
| *H01S 5/40* | (2006.01) | |
| *H01S 3/13* | (2006.01) | |
| *H01S 3/23* | (2006.01) | |
| *A61B 5/00* | (2006.01) | |

(52) U.S. Cl.
CPC ........ *H01S 5/4012* (2013.01); *A61B 5/0071* (2013.01); *A61B 5/0084* (2013.01); *A61B 5/6851* (2013.01); *H01S 3/1305* (2013.01); *H01S 3/23* (2013.01); *H01S 5/4025* (2013.01); *H01S 5/4087* (2013.01); *A61B 5/0075* (2013.01)

(58) Field of Classification Search
CPC .... H01S 5/4012; H01S 5/4025; H01S 5/4087; H01S 5/0683; A61B 5/0071; A61B 5/68451; A61B 5/0075; A61B 5/0084
See application file for complete search history.

(56) References Cited

U.S. PATENT DOCUMENTS

| | | | | |
|---|---|---|---|---|
| 6,066,096 A * | 5/2000 | Smith | .................... | A61B 8/12 128/916 |
| 7,519,096 B2 * | 4/2009 | Bouma | ................ | A61B 5/0059 372/102 |
| 8,874,230 B2 * | 10/2014 | Niver | .................... | A61B 90/37 606/33 |
| 10,058,284 B2 * | 8/2018 | Hoseit | ................. | A61B 5/6847 |
| 2002/0168317 A1 * | 11/2002 | Daighighian | .......... | A61K 49/18 424/1.11 |
| 2004/0199223 A1 * | 10/2004 | Andersen | ............... | A61B 18/22 607/89 |
| 2008/0281308 A1 * | 11/2008 | Neuberger | ............. | A61B 18/24 606/15 |
| 2009/0182225 A1 * | 7/2009 | Foley | .................... | A61B 18/24 600/424 |
| 2012/0033220 A1 * | 2/2012 | Kotidis | .................. | B82Y 20/00 356/445 |
| 2012/0059251 A1 * | 3/2012 | Bakker | ................ | A61B 5/0062 600/424 |
| 2015/0080712 A1 * | 3/2015 | Van Keersop | ....... | A61B 5/6848 600/424 |
| 2018/0342854 A1 * | 11/2018 | Shang | .................. | H01S 5/4087 |

* cited by examiner

*Primary Examiner* — Kinam Park
(74) *Attorney, Agent, or Firm* — Merchant & Gould P.C.

(57) ABSTRACT

The present invention provides an intervention photon control method and device, wherein the method comprises: a controller controls a multi-wavelength laser light source array to output a first group of laser, and the first group of laser is exported through an optical fiber, wherein the first group of laser comprises a laser of at least one wavelength; an optical fiber coupler couples the first group of laser which is exported by the optical fiber, to obtain a to-be-output laser; and an optical fiber guide wire sends the to-be-output laser to a to-be-analyzed tissue. Therefore, through the intervention photon control method and device provided by the present invention, the multi-wavelength laser light source array can be controlled through a controller, to provide laser for therapy, and the laser is guided to a lesion site via an optical fiber guide wire in a manner of subcutaneous puncture and artery or veinous intervention.

10 Claims, 2 Drawing Sheets

INTERVENTION PHOTON CONTROL METHOD AND DEVICE

TECHNICAL FIELD

The present invention relates to the field of interventional radiology, in particular to an intervention photon control method and device.

BACKGROUND ART

Photon diagnosis and photon therapy belong to two research and application development directions in the current medical photon technology, with the former taking a photon as an information carrier, and the latter taking a photon as an energy carrier. In photon diagnosis, identification of different tissues can be realized through performing real-time detection or imaging on reflected lights, transmission lights and scattered lights in the tissue or on fluorescent lights (including auto fluorescence and drug fluorescence) generated after a tissue is excited by an exciting light. In photon diagnosis, tissues are analyzed according to optical properties owned by a biological tissue. Compared with traditional surgical biopsy, photon diagnosis is a non-invasive histopathological analysis method, and can overcome a change in biochemical properties of tissues which may be caused in a surgical biopsy process; compared with such examinations as X-rays, CT and MRI, photon diagnosis can not only avoid ionizing radiation, but also realize early diagnosis of pathology. Photon therapy includes intense laser therapy, low-level (low-intensity) laser therapy and photodynamic therapy (PDT). With low-level laser radiation as an example, after an organism is radiated by a low-level laser, the laser does not directly cause an irreversible damage of a biological tissue, however, due to its own biological stimulus effect, a radiated tissue generates a "responsive" response to this stimulus. On a molecular level, synthesis of protein and nucleic acid is adjusted, replication of DNA is influenced, and the function of enzyme is adjusted; and on a cellular level, it is a process of removing pathology through mobilization, compensation, nutrition, repairing, immunity and other regenerative or defense mechanisms.

In recent years, along with an increasing maturity of nanotechnology and related interdisciplines, an application of the nanotechnology in medical science has revealed its importance for the first time. Many molecular markers which are applied to diagnostics and therapeutics respectively are integrated to form theranostics. Based on an important role of a photon technology in medical diagnosis and therapy, photonic theranostics, a brand-new research direction, is gradually formed, which is also a trend towards medical personalized development in the future. With photodynamic therapy (PDT) as an example, the target is to develop a nano particle platform which takes photosensitizer molecules as a core. The platform integrates active targeting delivery of medicines, diagnosis of tumors (such as MRI and molecular fluorescence imaging), therapy (hyperthermia therapy and PDT), dose monitoring (singlet oxygen probes and oxygen molecule probes), and therapeutic effect evaluation (cell apoptosis probes, MRI and biochemiluminescence), thereby fully reflecting advantages and potential applications of modern nanomedicine.

As an important means of diagnosis and therapy, the biggest drawback of photon is that visible lights and near-infrared lights cannot penetrate deep into human tissues, and now diagnosis and therapy can only be performed on a body surface and on surfaces of larger cavities of a human body (for example, esophagus). In order to solve the problem, a photon diagnosis and therapy device and method, which can penetrate deep into a human body and reach a lesion site and which will not cause greater damages to the human body, are needed.

SUMMARY OF THE INVENTION

The present invention aims at providing an intervention photon control method and device for overcoming the above problem or at least partially solving the above problem.

In order to achieve the above objective, technical solutions of the present invention are realized specifically as follows:

One aspect of the present invention provides an intervention photon control method, including: a controller controls a multi-wavelength laser light source array to output a first group of laser, and the first group of laser is exported through an optical fiber, wherein the first group of laser includes a laser of at least one wavelength; an optical fiber coupler couples the first group of laser which is exported by the optical fiber, to obtain a to-be-output laser; and an optical fiber guide wire sends the to-be-output laser to a to-be-analyzed tissue.

Wherein the method further includes: an optical fiber spectrograph acquires the to-be-output laser, generates spectral data of the to-be-output laser, and sends the spectral data of the to-be-output laser to the controller; and the controller receives the spectral data of the to-be-output laser, analyzes the spectral data of the to-be-output laser to obtain analysis results of the spectral data of the to-be-output laser, and outputs the analysis results of the spectral data of the to-be-output laser.

Wherein the method further includes: the optical fiber spectrograph acquires the to-be-output laser, generates the spectral data of the to-be-output laser, and sends the spectral data of the to-be-output laser to the controller; and the controller receives the spectral data of the to-be-output laser, analyzes the spectral data of the to-be-output laser to obtain analysis results of the spectral data of the to-be-output laser, and controls the multi-wavelength laser light source array to output a second group of laser according to analysis results of the spectral data of the to-be-output laser, wherein the second group of laser includes a laser of at least one wavelength.

Wherein the method further includes: the optical fiber guide wire receives a feedback fluorescence which is absorbed by a to-be-analyzed tissue, and sends the feedback fluorescence to an optical fiber spectrograph through the optical fiber coupler; the optical fiber spectrograph acquires the feedback fluorescence, generates spectral data of the feedback fluorescence, and sends the spectral data of the feedback fluorescence to the controller; and the controller receives the spectral data of the feedback fluorescence, analyzes the spectral data of the feedback fluorescence to obtain analysis results of the feedback fluorescence, and outputs analysis results of the feedback fluorescence.

Wherein the method further includes: the optical fiber guide wire receives a feedback fluorescence which is absorbed by a to-be-analyzed tissue, and sends the feedback fluorescence to an optical fiber spectrograph through the optical fiber coupler; the optical fiber spectrograph acquires the feedback fluorescence, generates spectral data of the feedback fluorescence, and sends the spectral data of the feedback fluorescence to the controller; and the controller receives the spectral data of the feedback fluorescence, analyzes the spectral data of the feedback fluorescence to obtain analysis results of the feedback fluorescence, and controls the multi-wavelength laser light source array to output a third group of laser according to analysis results of the feedback fluorescence, wherein the third group of laser includes a laser of at least one wavelength.

Another aspect of the present invention provides an intervention photon control device, including: a controller, configured to control a multi-wavelength laser light source array to output a first group of laser, wherein the first group of laser is exported through an optical fiber, and the first group of laser includes a laser of at least one wavelength; an optical fiber coupler, configured to couple the first group of laser which is exported by the optical fiber, to obtain a to-be-output laser; and an optical fiber guide wire, configured to send the to-be-output laser to a to-be-analyzed tissue.

Wherein the device further includes an optical fiber spectrograph; the optical fiber spectrograph is configured to acquire the to-be-output laser, generate spectral data of the to-be-output laser, and send the spectral data of the to-be-output laser to the controller; the controller is further configured to receive the spectral data of the to-be-output laser, analyze the spectral data of the to-be-output laser to obtain analysis results of the spectral data of the to-be-output laser, and output the analysis results of the spectral data of the to-be-output laser.

Wherein the device further includes an optical fiber spectrograph; the optical fiber spectrograph is configured to acquire the to-be-output laser, generate spectral data of the to-be-output laser, and send the spectral data of the to-be-output laser to the controller; and the controller is further configured to receive the spectral data of the to-be-output laser, analyze the spectral data of the to-be-output laser to obtain analysis results of the spectral data of the to-be-output laser, and control the multi-wavelength laser light source array to output a second group of laser according to analysis results of the spectral data of the to-be-output laser, wherein the second group of laser includes a laser of at least one wavelength.

Wherein the device further includes an optical fiber spectrograph; the optical fiber guide wire is further configured to receive a feedback fluorescence which is absorbed by a to-be-analyzed tissue, and send the feedback fluorescence to an optical fiber spectrograph through the optical fiber coupler; the optical fiber spectrograph is configured to acquire the feedback fluorescence, generate spectral data of the feedback fluorescence, and send the spectral data of the feedback fluorescence to the controller; and the controller is further configured to receive the spectral data of the feedback fluorescence, analyze the spectral data of the feedback fluorescence to obtain analysis results of the feedback fluorescence, and output analysis results of the feedback fluorescence.

Wherein the device further includes an optical fiber spectrograph; the optical fiber guide wire is further configured to receive a feedback fluorescence which is absorbed by a to-be-analyzed tissue, and send the feedback fluorescence to an optical fiber spectrograph through the optical fiber coupler; the optical fiber spectrograph is configured to acquire the feedback fluorescence, generate spectral data of the feedback fluorescence, and send the spectral data of the feedback fluorescence to the controller; and the controller is further configured to receive the spectral data of the feedback fluorescence, analyze the spectral data of the feedback fluorescence to obtain analysis results of the feedback fluorescence, and control the multi-wavelength laser light source array to output a third group of laser according to analysis results of the feedback fluorescence, wherein the third group of laser includes a laser of at least one wavelength.

Therefore, it can be seen that, through the intervention photon control method and device provided by the present invention, the multi-wavelength laser light source array can be controlled through a controller, to provide a laser for therapy, and the laser is guided to a lesion site via an optical fiber guide wire in a manner of subcutaneous puncture and artery or veinous intervention.

Further, spectral data, of a laser output by a multi-wavelength laser light source array, output via an optical fiber spectrograph can be analyzed, and the analysis results can be output, so as to facilitate follow-up view and analysis of medical staff.

Or, spectral data, of a laser output by a multi-wavelength laser light source array, output via an optical fiber spectrograph can be received by a controller, the spectral data can be processed and analyzed, and lasers of different wavelengths for illumination therapy can be provided according to different conditions;

or, a controller processes and analyzes spectral data of a feedback fluorescence output by an optical fiber spectrograph, and analysis results of a laser fed back by a lesion are output, so as to facilitate follow-up view and analysis of medical staff;

or, a controller processes and analyzes spectral data of a feedback fluorescence output by an optical fiber spectrograph, and based on analysis results of lasers fed back by a lesion, lasers of different wavelengths for illumination therapy can be provided according to different conditions.

BRIEF DESCRIPTION OF THE DRAWINGS

In order to more clearly describe technical solutions of embodiments of the present invention, a brief introduction will be made to the accompanying drawings which need to be used in the description of the embodiments. Apparently, the accompanying drawings described below are merely some embodiments of the present invention, and for those skilled in the art, other accompanying drawings can be obtained based on these accompanying drawings without any creative effort.

DETAILED DESCRIPTION OF THE EMBODIMENTS

In combination with accompanying drawings, it should be understood that, the present disclosure can be realized in various forms, and should not be limited by embodiments described herein. In contrary, these embodiments are provided for a more thorough understanding of the present disclosure, and can completely convey the scope of the present disclosure to those skilled in the art.

Figure 1:
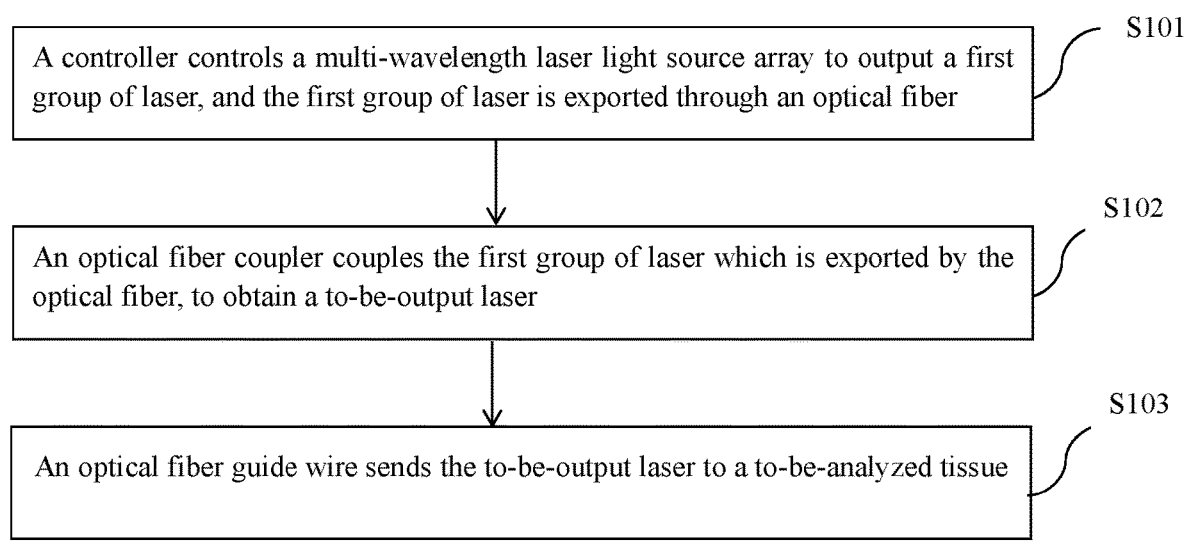
FIG. 1 is a flow chart of an intervention photon control method provided by an embodiment of the present invention.

FIG. 1 shows a flow chart of an intervention photon control method provided by an embodiment of the present invention. Please refer to FIG. 1, and an intervention photon control method provided by an embodiment of the present invention includes:

S101, a controller controls a multi-wavelength laser light source array to output a first group of laser, and the first group of laser is exported through an optical fiber, wherein the first group of laser includes a laser of at least one wavelength;

S102, an optical fiber coupler couples the first group of laser which is exported by the optical fiber, to obtain a to-be-output laser; and S103, an optical fiber guide wire sends the to-be-output laser to a to-be-analyzed tissue.

Specifically, a device for providing an intervention photon control method provided by an embodiment of the present invention is arranged. The device can mainly include a controller, a multi-wavelength laser light source array, an optical fiber coupler and a blood vessel optical fiber guide wire. Further, the device can further include an optical fiber spectrograph. The device controls a multi-wavelength laser light source array to provide a light source for diagnosis and therapy through a controller, and couples photons from multi-wavelength laser light source array respectively through an optical fiber coupler, the laser is then guided to a lesion site via an optical fiber guide wire in a manner of subcutaneous puncture and artery or veinous intervention, and then the multi-wavelength laser light source array is controlled through a controller, so as to realize illumination therapy.

Wherein the multi-wavelength laser light source array can contain multiple laser devices which can emit multiple wavelengths, for example, the wavelengths are respectively 532 nm, 630 nm and 650 nm, so as to be adapted to diagnosis and therapy of different diseases.

One construction mode of an optical fiber coupler is a two-level structure, wherein a first level of structure is a structure which unifies N into one (N is greater than or equal to 2), that is, N optical fibers which respectively transmit N laser wavelengths are coupled to one optical fiber; and a second level of structure is a structure which unifies two into one, that is, lasers of multiple wavelengths and optical fibers of a spectrograph are coupled to one optical fiber; and the connected optical fiber guide wire is internally provided with an optical fiber core wire. During specific applications, a multi-wavelength laser light source array can be constituted by three semiconductor laser devices of 630 nm, 650 nm and 670 nm respectively, and is output by an optical fiber in a coupling manner. An optical fiber guide wire has an external diameter of 400 μm, is internally provided with four optical fiber core wires with a diameter of 50 μm, and the outer layer is wrapped with stainless metal tubes with spiral slits. The above metal tube is externally coated with a hydrophilic coating, for example, polytetrafluoroethylene, silicone rubber, polyethylene, polyvinyl chloride, fluorocarbon polymer and polyurethane. The optical fiber guide wire is connected with a multi-wavelength laser light source array and an optical fiber spectrograph through an optical fiber coupler, three optical fiber core wires wrapped by optical fiber guide wires are respectively connected with three laser devices in three multi-wavelength laser light source arrays, while another optical fiber core wire is connected with an optical fiber spectrograph. The lasers output by a laser device are emitted through three optical fiber core wires inside the optical fiber guide wire, and are collected by another optical fiber core wire and transmitted back to a spectrograph.

Another construction mode of an optical fiber coupler is a one-level structure, wherein N optical fibers (N is greater than or equal to 2) of N laser wavelengths are respectively transmitted and are coupled to an optical fiber guide wire. Among the N optical fibers, N−1 optical fibers are optical fibers output by a multi-wavelength laser array, and one optical fiber is an optical fiber of an optical fiber spectrograph; and the connected optical fiber guide wire is internally provided with N optical fiber core wires. During specific applications, a multi-wavelength laser light source array can be constituted by three semiconductor laser devices of 630 nm, 650 nm and 670 nm respectively, and is output by an optical fiber in a coupling manner. An optical fiber guide wire has an external diameter of 400 μm, is internally provided with one optical fiber core wire with a diameter of 300 μm, and the outer layer is wrapped with stainless metal tubes with spiral slits. The above metal tube is externally coated with a hydrophilic coating, for example, polytetrafluoroethylene, silicone rubber, polyethylene, polyvinyl chloride, fluorocarbon polymer and polyurethane. The optical fiber guide wire is connected with a multi-wavelength laser light source array and an optical fiber spectrograph through an optical fiber coupler, three laser devices are coupled to one optical fiber through an optical fiber coupler, and then is coupled to one optical fiber with an optical fiber of the optical fiber spectrograph, and is connected with an optical fiber core wire in the optical fiber guide wire. The lasers output by a laser device are emitted through one optical fiber core wire inside the optical fiber guide wire, and are collected by the same optical fiber core wire and transmitted back to an optical fiber spectrograph.

An optical fiber guide wire plays a role of performing unidirectional and/or bidirectional transmission of photons (for example, the to-be-output laser in an optical fiber guide wire and feedback fluorescence are subjected to parallel unidirectional transmission by multiple optical fiber core wires; or the to-be-output laser in an optical fiber guide wire and feedback fluorescence are subjected to bidirectional transmission by one optical fiber core wire). Meanwhile, the optical fiber guide wire can penetrate through a vascular tunnel, and has a proper strength and flexibility, thereby avoiding optical fiber breakage inside the human body or avoiding damage to human tissues. The optical fiber guide wire has a diameter of 50 μm to 500 μm and a length of 0.5 m to 2 m. The light function guide wire is internally provided with optical fibers, meshy or spirally incised metal materials are wrapped outside the light function guide wire, and a hydrophilic or hydrophobic coating is coated on the outermost layer, so as to increase blood compatibility.

An optical fiber spectrograph can be added with a wave filter, so as to filter wavelengths of an output laser, and improve sensitivity in collecting fluorescence wavelengths.

During specific applications, firstly, an optical fiber guide wire passes through an artery or vein via subcutaneous puncture, and is guided to a lesion site inside a human body under guidance of radiological imaging. An illumination wavelength is selected, a controller selects a specific laser device in a multi-wavelength laser light source array to output, and the illumination time is set. A controller controls output of the laser, the laser is conducted to an optical fiber guide wire through an optical fiber coupler, and illumination reaches a lesion site through an optical fiber guide wire. After the set time finishes, illumination stops, and the therapy process is completed.

Therefore, it can be seen that, through the intervention photon control method provided by the present invention, the multi-wavelength laser light source array can be controlled through a controller, to provide a laser for therapy, and the laser is guided to a lesion site via an optical fiber guide wire in a manner of subcutaneous puncture and artery or veinous intervention.

As an optional implementation of an embodiment of the present invention, the intervention photon control method further includes: an optical fiber spectrograph acquires a to-be-output laser, generates spectral data of the to-be-output laser, and sends the spectral data of the to-be-output laser to a controller; the controller receives the spectral data of the to-be-output laser, analyzes the spectral data of the to-be-output laser to obtain analysis results of the spectral data of the to-be-output laser, and outputs the analysis results of the spectral data of the to-be-output laser. Specifically, an optical fiber spectrograph can be utilized to acquire a to-be-output laser and generate spectral data of the to-be-output laser, such that the controller can analyze and output analysis results. Therefore, spectral data, of a laser output by a multi-wavelength laser light source array, output via an optical fiber spectrograph can be analyzed, and the analysis results can be output, so as to facilitate follow-up view and analysis of medical staff. During specific applications, firstly, an optical fiber guide wire passes through an artery or vein via subcutaneous puncture, and is guided to a lesion site inside a human body under guidance of radiological imaging. An illumination wavelength is selected, a controller selects a specific laser device in a multi-wavelength laser light source array to output, and meanwhile the controller controls a spectrograph to receive spectrum. A laser, output through a specific laser device in a multi-wavelength laser light source array, is conducted to an optical fiber guide wire through an optical fiber coupler, illumination reaches a lesion site through the optical fiber guide wire, spectral data of a laser output by a specific laser in a multi-wavelength laser light source array is analyzed, and then analysis results are output and for example are displayed, so as to facilitate follow-up view and analysis of medical staff.

As an optional implementation of an embodiment of the present invention, intervention photon control further includes: an optical fiber spectrograph acquires a to-be-output laser, generates spectral data of the to-be-output laser, and sends the spectral data of the to-be-output laser to a controller; and the controller receives the spectral data of the to-be-output laser, analyzes the spectral data of the to-be-output laser to obtain analysis results of the spectral data of the to-be-output laser, and controls the multi-wavelength laser light source array to output a second group of laser according to analysis results of the spectral data of the to-be-output laser, wherein the second group of laser includes a laser of at least one wavelength. Specifically, an optical fiber spectrograph can be utilized to acquire a to-be-output laser and generate spectral data of the to-be-output laser, such that the controller can analyze, and control and adjust the laser output by a multi-wavelength laser light source array according to analysis results. Therefore, spectral data, of a laser output by a multi-wavelength laser light source array, output via an optical fiber spectrograph can be received by a controller, the spectral data can be processed and analyzed, and lasers of different wavelengths for illumination therapy can be provided according to different conditions. During specific applications, firstly, an optical fiber guide wire passes through an artery or vein via subcutaneous puncture, and is guided to a lesion site inside a human body under guidance of radiological imaging. An illumination wavelength is selected, a controller selects a specific laser device in a multi-wavelength laser light source array to output, and the controller controls a spectrograph to receive spectrum. A laser, output through a specific laser device in a multi-wavelength laser light source array, is conducted to an optical fiber guide wire through an optical fiber coupler, illumination reaches a lesion site through the optical fiber guide wire, spectral data of a laser output by a specific laser in a multi-wavelength laser light source array is analyzed, and then a specific laser device in the multi-wavelength laser light source array can be controlled to output a more proper laser according to analysis results.

As an optional implementation of an embodiment of the present invention, intervention photon control further includes: the optical fiber guide wire receives a feedback fluorescence which is absorbed by a to-be-analyzed tissue, and sends the feedback fluorescence to an optical fiber spectrograph through the optical fiber coupler; the optical fiber spectrograph acquires the feedback fluorescence, generates spectral data of the feedback fluorescence, and sends the spectral data of the feedback fluorescence to the controller; and the controller receives the spectral data of the feedback fluorescence, analyzes the spectral data of the feedback fluorescence to obtain analysis results of the feedback fluorescence, and outputs analysis results of the feedback fluorescence. Specifically, an optical fiber spectrograph can be utilized to acquire a feedback fluorescence which is absorbed by a to-be-analyzed tissue, and generate spectral data of the feedback fluorescence which is absorbed by the to-be-analyzed tissue, such that the controller can analyze and output analysis results. Therefore, a controller processes and analyzes spectral data of a feedback fluorescence output by an optical fiber spectrograph, and analysis results of a laser fed back by a lesion are output, so as to facilitate follow-up view and analysis of medical staff. During specific applications, firstly, an optical fiber guide wire passes through an artery or vein via subcutaneous puncture, and is guided to a lesion site inside a human body under guidance of radiological imaging. An illumination wavelength is selected, and a controller selects a specific laser device in a multi-wavelength laser light source array to output. A laser, output through a specific laser device in a multi-wavelength laser light source array, is conducted to an optical fiber guide wire through an optical fiber coupler, illumination reaches a lesion site through the optical fiber guide wire, meanwhile, a controller controls a spectrograph to receive a spectrum of a laser reflected after a lesion site absorbs light. Spectral data of a laser reflected after a lesion site absorbs light is analyzed, and then analysis results are output and for example are displayed, so as to facilitate follow-up view and analysis of medical staff.

As an optional implementation of an embodiment of the present invention, intervention photon control further includes: the optical fiber guide wire receives feedback fluorescence which is absorbed by a to-be-analyzed tissue, and sends the feedback fluorescence to an optical fiber spectrograph through the optical fiber coupler; the optical fiber spectrograph acquires the feedback fluorescence, generates spectral data of the feedback fluorescence, and sends the spectral data of the feedback fluorescence to a controller; and the controller receives the spectral data of the feedback fluorescence, analyzes the spectral data of the feedback fluorescence to obtain analysis results of the feedback fluorescence, and controls the multi-wavelength laser light source array to output a third group of laser according to analysis results of the feedback fluorescence, wherein the third group of laser includes a laser of at least one wavelength. Specifically, an optical fiber spectrograph can be utilized to acquire a feedback fluorescence which is absorbed by a to-be-analyzed tissue, and generate spectral data of the feedback fluorescence which is absorbed by the to-be-analyzed tissue, such that the controller can analyze and control and adjust the laser output by the multi-wavelength laser light source array according to analysis results. Therefore, a controller processes and analyzes spectral data of a feedback fluorescence output by an optical fiber spectrograph, and based on analysis results of a laser fed back by a lesion, lasers of different wavelengths for illumination therapy can be provided according to different conditions. During specific applications, firstly, an optical fiber guide wire passes through an artery or vein via subcutaneous puncture, and is guided to a lesion site inside a human body under guidance of radiological imaging. An illumination wavelength is selected, a controller selects a specific laser device in a multi-wavelength laser light source array to output. A laser, output through a specific laser device in a multi-wavelength laser light source array, is conducted to an optical fiber guide wire through an optical fiber coupler. Illumination reaches a lesion site through the optical fiber guide wire, meanwhile, a controller controls a spectrograph to receive a spectrum of a laser reflected after a lesion site absorbs light. Spectral data of a laser reflected after a lesion site absorbs light is analyzed, and then a specific laser device in the multi-wavelength laser light source array can be controlled to output a more proper laser according to analysis results.

Two specific embodiments will be provided below to describe an intervention photon control method provided by embodiments of the present invention, however, the present invention is not limited hereto:

Embodiment 1

With intravascular photodynamic tumor treatment as an example, if a patient suffers from liver cancer, the patient is firstly injected with photosensitive drugs, for example, photophrin, and after keeping out of the sun for a period of time, photosensitizers are concentrated on the tumor site in the liver. Through percutaneous puncture on a blood vessel and under the guidance of clinical imaging, an optical fiber guide wire is inserted inside a tumor inside a liver. A laser with an excitation wavelength of 630 nm of photosensitizers in a multi-wavelength laser light source array is selected to emit light, and an optical fiber guide wire guides a laser of 630 nm to enter inside a tumor concentrated with photosensitive drugs, such that the photosensitive drugs inside the tumor are subjected to a photochemical reaction to generate singlet oxygen, and then lead to necrosis and apoptosis of the tumor. When a novel photosensitizer is used for therapy, for example, tetrahydroxybenzene chloride (m-THPC), the absorption peak is at 650 nm, a controller is used to select a laser device of 650 nm to emit light, and the other steps are similar to the above steps.

Embodiment 2

With fluorescence diagnosis as an example, through percutaneous puncture of a blood vessel and under guidance of clinical imaging, an optical fiber guide wire passes through a blood vessel and is guided to a lesion site. A laser device of 630 nm in a multi-wavelength laser light source array is selected by a controller to emit light. The laser passes through the optical fiber guide wire and irradiates on a lesion tissue, and the generated fluorescence is collected by an optical fiber guide wire and is transmitted back to an optical fiber spectrograph. Such feature parameters as peak wavelength of fluorescence emission, relative fluorescence strength and fluorescence spectrum width can be obtained through data of an optical fiber spectrograph. Laser devices of other wavelengths in the multi-wavelength laser light source array can also be selected by a controller to emit light and the above steps are repeated, then excitation characteristics of fluorescence with different wavelengths can be obtained.

Figure 2:
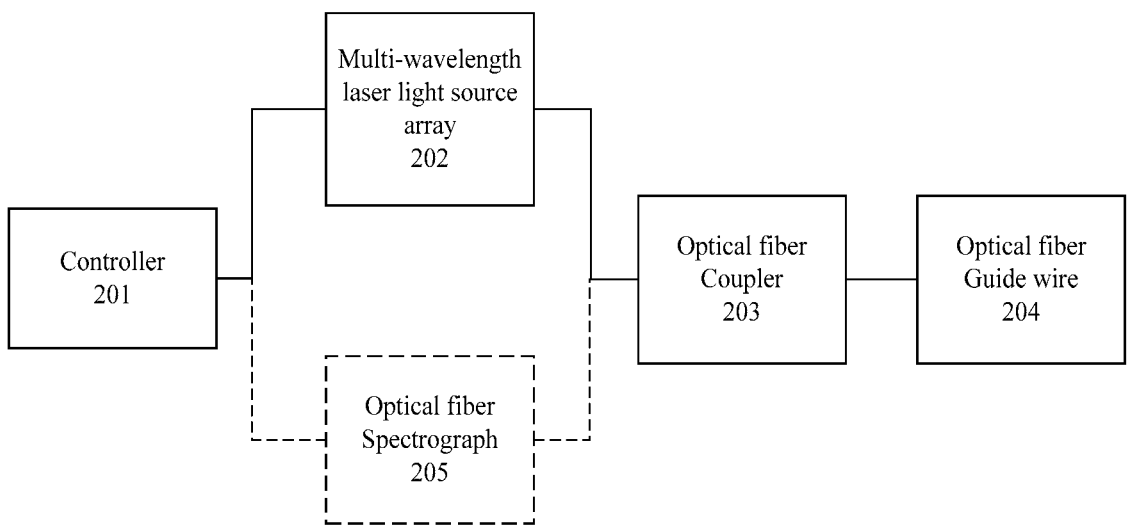
FIG. 2 is a structural schematic diagram of an intervention photon control device provided by an embodiment of the present invention.

FIG. 2 shows a structural schematic diagram of an intervention photon control device provided by an embodiment of the present invention. The intervention photon control device is applied to the above method. Only the structure of the intervention photon control device is described simply below, and for the other contents which are not described in detail, please refer to related descriptions in the above intervention photon control method. Please refer to FIG. 2, and an intervention photon control device provided by an embodiment of the present invention includes:

a controller 201, configured to control a multi-wavelength laser light source array 202 to output a first group of laser, wherein the first group of laser is exported through an optical fiber, and the first group of laser includes a laser of at least one wavelength;

an optical fiber coupler 203, configured to couple the first group of laser which is exported by the optical fiber, to obtain a to-be-output laser; and an optical fiber guide wire 204, configured to send the to-be-output laser to a to-be-analyzed tissue.

Therefore, it can be seen that, through the intervention photon control device provided by the present invention, the multi-wavelength laser light source array can be controlled through a controller, to provide a laser for therapy, and the laser is guided to a lesion site via an optical fiber guide wire in a manner of subcutaneous puncture and artery or venous intervention.

As an optional implementation of an embodiment of the present invention, the intervention photon control device further includes an optical fiber spectrograph 205; the optical fiber spectrograph 205 is configured to acquire the to-be-output laser, generate spectral data of the to-be-output laser, and send the spectral data of the to-be-output laser to the controller 201; and the controller 201 is further configured to receive the spectral data of the to-be-output laser, analyze the spectral data of the to-be-output laser to obtain analysis results of the spectral data of the to-be-output laser, and output the analysis results of the spectral data of the to-be-output laser, therefore, spectral data, of a laser output by a multi-wavelength laser light source array, output via an optical fiber spectrograph can be analyzed, and the analysis results can be output, so as to facilitate follow-up view and analysis of medical staff.

As an optional implementation of an embodiment of the present invention, an intervention photon control device further includes an optical fiber spectrograph 205; the optical fiber spectrograph 205 is configured to acquire the to-be-output laser, generate spectral data of the to-be-output laser, and send the spectral data of the to-be-output laser to the controller 201; and the controller 201 is further configured to receive the spectral data of the to-be-output laser, analyze the spectral data of the to-be-output laser to obtain analysis results of the spectral data of the to-be-output laser, and control the multi-wavelength laser light source array to output a second group of laser according to analysis results of the spectral data of the to-be-output laser, wherein the second group of laser includes a laser of at least one wavelength. Therefore, spectral data, of a laser output by a multi-wavelength laser light source array, output via an optical fiber spectrograph can be received by a controller, the spectral data can be processed and analyzed, and lasers of different wavelengths for illumination therapy can be provided according to different conditions.

As an optional implementation of an embodiment of the present invention, an intervention photon control device further includes an optical fiber spectrograph 205; the optical fiber guide wire 204 is further configured to receive a feedback fluorescence which is absorbed by a to-be-analyzed tissue, and send the feedback fluorescence to an optical fiber spectrograph 205 through the optical fiber coupler; the optical fiber spectrograph 205 is configured to acquire the feedback fluorescence, generate spectral data of the feedback fluorescence, and send the spectral data of the feedback fluorescence to the controller 201; and the controller 201 is further configured to receive the spectral data of the feedback fluorescence, analyze the spectral data of the feedback fluorescence to obtain analysis results of the feedback fluorescence, and output analysis results of the feedback fluorescence. Therefore, a controller processes and analyzes spectral data of a feedback fluorescence output by an optical fiber spectrograph, and analysis results of a laser fed back by a lesion are output, so as to facilitate follow-up view and analysis of medical staff.

As an optional implementation of an embodiment of the present invention, an intervention photon control device further includes an optical fiber spectrograph 205; the optical fiber guide wire 204 is further configured to receive a feedback fluorescence which is absorbed by a to-be-analyzed tissue, and send the feedback fluorescence to an optical fiber spectrograph 205 through the optical fiber coupler; the optical fiber spectrograph 205 is configured to acquire the feedback fluorescence, generate spectral data of the feedback fluorescence, and send the spectral data of the feedback fluorescence to the controller 201; and the controller 201 is further configured to receive the spectral data of the feedback fluorescence, analyze the spectral data of the feedback fluorescence to obtain analysis results of the feedback fluorescence, and control the multi-wavelength laser light source array to output a third group of laser according to analysis results of the feedback fluorescence, wherein the third group of laser includes a laser of at least one wavelength. Therefore, a controller processes and analyzes spectral data of a feedback fluorescence output by an optical fiber spectrograph, and based on analysis results of lasers fed back by a lesion, lasers of different wavelengths for illumination therapy can be provided according to different conditions.

Those skilled in the art should understand that, embodiments of the present application can be provided as methods, systems, or computer program products. Therefore, the present application can be an entirely hardware embodiment, an entirely software embodiment, or an embodiment combining software and hardware. Moreover, the present application can adopt a form of computer program products which can be implemented on one or more computer available storage mediums (which include but are not limited to a disk memory, CD-ROM, and an optical memory) which include computer available program codes.

The application has been described in a flow chart and/or a block diagram of the method, the device (system) and the computer program product according to the embodiments of the application. It shall be appreciated that respective flows and/or blocks in the flow chart and/or the block diagram and combinations of the flows and/or the blocks in the flow chart and/or the block diagram can be embodied in computer program instructions. These computer program instructions can be loaded onto a general-purpose computer, a specific-purpose computer, an embedded processor or a processor of another programmable data processing device to produce a machine so that the instructions executed on the computer or the processor of the other programmable data processing device create means for performing the functions specified in the flow(s) of the flow chart and/or the block(s) of the block diagram.

These computer program instructions can also be stored into a computer readable memory capable of directing the computer or the other programmable data processing device to operate in a specific manner, so that the instructions stored in the computer readable memory create an article of manufacture including instruction means which perform the functions specified in the flow(s) of the flow chart and/or the block(s) of the block diagram.

These computer program instructions can also be loaded onto the computer or the other programmable data processing device, so that a series of operational steps are performed on the computer or the other programmable data processing device to create a computer implemented process, so that the instructions executed on the computer or the other programmable device provide steps for performing the functions specified in the flow(s) of the flow chart and/or the block(s) of the block diagram.

In a typical configuration, a computing device includes one or more central processing units (CPU), an input/output interface, a network interface and an internal storage.

A storage can possibly include a volatile memory, a random access memory (RAM), and/or a non-volatile memory in a computer readable medium, such as a read only memory (ROM) or a flash memory (flash RAM). A storage is an example of a computer readable medium.

Computer readable media includes permanent and non-permanent media and mobile and non-mobile media, and information storage can be realized through any method or technique. Information can be computer readable instructions, data structures, modules of programs or other data. Storage media of a computer for example include but are not limited to: a phase change memory (PRAM), a static random access memory (SRAM), a dynamic random access memory (DRAM), other types of random access memories (RAM), a read-only memory (ROM), an electrically erasable programmable read-only memory (EEPROM), a flash memory or other memory techniques, a compact disc read-only memory (CD-ROM), a digital versatile disc (DVD) or other types of optical storage, and a cassette tape. Tape and disc storage devices or other magnetic storage devices or any other non-transmission media can be used to store information accessed by a computing device. As defined in the text, the computer readable media do not include transitory media, such as modulated data signals and carriers.

What is described above is merely embodiments of the present application, and is not used for limiting the present application. For those skilled in the art, various alterations and changes can be made to the present application. Any modifications, equivalent substitutions and improvements made within the spirit and principle of the present application shall all fall within the scope of claims of the present application.

I claim:

1. An intervention photon control method, comprising:
   controlling a multi-wavelength laser light source array to output a first group of laser, wherein the first group of laser comprises a laser of at least one wavelength;
   transmitting the output of the first group of laser with an optical fiber coupler, thereby establishing a to-be-output laser;
   transmitting the to-be-output laser via an optical fiber guide wire to a to-be-analyzed tissue, whereby a feedback florescence is emitted by the tissue; and performing at least one of the following with an optical fiber spectrograph:
   i) generating spectral data of the to-be-output laser and sending the spectral data of the to-be-output laser to a controller; and
   ii) acquiring the feedback fluorescence from the optical fiber guide wire and the optical fiber coupler, generating spectral data of the feedback fluorescence, and sending the spectral data of the feedback fluorescence to the controller.

2. The method of claim 1, further comprising:
analyzing the spectral data of the to-be-output laser and outputting the analysis results of the spectral data of the to-be-output laser.

3. The method of claim 1, further comprising:
analyzing the spectral data of the to-be-output laser to obtain analysis results of the spectral data of the to-be-output laser, and
controlling the multi-wavelength laser light source array to output a second group of laser according to the analysis results of the spectral data of the to-be-output laser, wherein the second group of laser comprises a laser of at least one wavelength.

4. The method of claim 1, further comprising:
receiving the spectral data of the feedback fluorescence, analyzing the spectral data of the feedback fluorescence to obtain analysis results of the feedback fluorescence, and outputting analysis results of the feedback fluorescence.

5. The method of claim 1, further comprising:
receiving the spectral data of the feedback fluorescence by the controller, analyzing the spectral data of the feedback fluorescence to obtain analysis results of the feedback fluorescence, and controlling the multi-wavelength laser light source array to output a third group of laser according to analysis results of the feedback fluorescence, wherein the third group of laser comprises a laser of at least one wavelength.

6. An intervention photon control device, comprising:
a controller, configured to control a multi-wavelength laser light source array to output a first group of laser, wherein the first group of laser is exported through an optical fiber, and the first group of laser comprises a laser of at least one wavelength;
an optical fiber coupler, configured to couple the first group of laser which is exported by the optical fiber, to obtain a to-be-output laser;
an optical fiber guide wire, configured to send the to-be-output laser to a to-be-analyzed tissue, whereby a feedback florescence is emitted by the tissue; and
an optical fiber spectrograph arranged and configured to perform at least one of the following:
   i) acquire the to-be-output laser, generate spectral data of the to-be-output laser, and send the spectral data of the to-be-output laser to the controller; and
   ii) acquire the feedback fluorescence, generate spectral data of the feedback fluorescence, and send the spectral data of the feedback fluorescence to the controller.

7. The device of claim 6, wherein
the controller is further configured to receive the spectral data of the to-be-output laser, analyze the spectral data of the to-be-output laser to obtain analysis results of the spectral data of the to-be-output laser, and output the analysis results of the spectral data of the to-be-output laser.

8. The device of claim 6, wherein
the controller is further configured to receive the spectral data of the to-be-output laser, analyze the spectral data of the to-be-output laser to obtain analysis results of the spectral data of the to-be-output laser, and control the multi-wavelength laser light source array to output a second group of laser according to analysis results of the spectral data of the to-be-output laser, wherein the second group of laser comprises a laser of at least one wavelength.

9. The device of claim 6, wherein
the controller is further configured to receive the spectral data of the feedback fluorescence, analyze the spectral data of the feedback fluorescence to obtain analysis results of the feedback fluorescence, and output analysis results of the feedback fluorescence.

10. The device of claim 6, wherein
the controller is further configured to receive the spectral data of the feedback fluorescence, analyze the spectral data of the feedback fluorescence to obtain analysis results of the feedback fluorescence, and control the multi-wavelength laser light source array to output a third group of laser according to analysis results of feedback fluorescence, wherein the third group of laser comprises a laser of at least one wavelength.

* * * * *